United States Patent [19]

Shinoda et al.

[11] Patent Number: 4,478,995
[45] Date of Patent: Oct. 23, 1984

[54] COMPLEX COMPOUNDS

[75] Inventors: Masamitu Shinoda, Minou; Ikuo Tanaka, Minou; Tadahiko Yasuda, Kyoto; Isao Nakajima, Toyonaka; Tutomu Adachi, Itami; Giichi Ikeda, Kyoto, all of Japan

[73] Assignee: Teikoku Chemical Industry Co., Ltd., Osaka, Japan

[21] Appl. No.: 412,972

[22] Filed: Aug. 27, 1982

[30] Foreign Application Priority Data

Sep. 1, 1981 [JP] Japan .................................. 56/138048

[51] Int. Cl.³ ............................................. C08B 37/16
[52] U.S. Cl. ...................................... 536/46; 424/180
[58] Field of Search .......................... 536/46; 424/180

[56] References Cited

U.S. PATENT DOCUMENTS 3,869,443 3/1975 Lesher .................................... 536/46
4,258,180 3/1981 Lewis et al. ........................ 424/180

OTHER PUBLICATIONS

Dissertation Abstracts International B, Dec. 1980, vol. 41, No. 6, p. 2127.
Chemical Abstracts, vol. 95, No. 4, Jul. 27, 1981, Abstract No. 95:31250x.
Chemical Abstracts, vol. 95, No. 17, Oct. 26, 1981, Abstract No. 95:150111n.
Chemical Abstracts, vol. 95, No. 26, Dec. 28, 1981, Abstract No. 95:224668y.

*Primary Examiner*—Ronald W. Griffin
*Attorney, Agent, or Firm*—Wenderoth, Lind & Ponack

[57] ABSTRACT

A complex of an acid addition salt of (2'-benzyloxycarbonyl)phenyl trans-4-guanidinomethylcyclohexanecarboxylate and a cyclodextrin. The complex is useful for the treatment of ulcers.

8 Claims, 4 Drawing Figures

COMPLEX COMPOUNDS

FIELD OF INVENTION

The present invention relates to a novel complex compound obtained from the combination of an acid addition salt of (2'-benzyloxycarbonyl)phenyl trans-4-guanidinomethylcyclohexanecarboxylate and a cyclodextrin.

BACKGROUND OF INVENTION

Since an acid addition salt of (2'-benzyloxycarbonyl)phenyl trans-4-guanidinomethylcyclohexanecarboxylate (hereinafter abbreviated as GCP acid addition salt) has the properties of inhibiting activities of proteolytic enzymes such as Trypsin, Chymotrypsin, Thrombin, Callicrein, Urokinase and the like, great hopes are entertained of the compound as a medicine. However, this has only limited absorption and hence it is essential to administer a larger quantity, which has obstructed the practical use thereof to this day.

One of the most interesting possible applications of this compound would be in the area of ulcer treatment in connection with the abovementioned enzyme-activity inhibiting properties. This, of course, would be on condition that the main ingredient be absorbed well with a common administration dosage thereof.

As the results of our extensive studies, the inventors have found that the novel complex of the abovementioned GCP acid addition salt with cyclodextrin has an excellent solubility in water, is well absorbed through the digestive tract, and is very effective for the control of ulcer symptoms. On the basis of these findings, the inventors have completed the invention.

SUMMARY OF THE INVENTION

This invention provides a complex of an acid addition salt of (2'-benzyloxycarbonyl)phenyl trans-4-guanidinomethylcyclohexanecarboxylate with cyclodextrin. It also provides a pharmaceutical composition containing the same.

DESCRIPTION OF SPECIFIC EMBODIMENTS

The novel complex compounds of the present invention are provided by the interaction of an acid addition salt of (2'-benzyloxycarbonyl)phenyl trans-4-guanidinomethylcyclohexanecarboxylate with cyclodextrin. They are easily obtained as follows:

That is, GCP acid addition salt and cyclodextrin are added to water, optionally heated with stirring to assist dissolution, and thus obtained solution is subjected, according to normal procedure, to freeze-drying or concentration to separate the complex compound thus formed.

As the GCP acid addition salt, mention is made of such members as hydrochloride, hydrobromide, hydroiodide, carbonate, acetate, sulfate, p-toluenesulfonate, methanesulfonate, lactate, maleate, fumarate, tartarate and citrate of GCP. As cyclodextrin useable in the invention, mention is made of $\alpha$-cyclodextrin, $\beta$-cyclodextrin, and $\gamma$-cyclodextrin. Among them, most preferable is $\beta$-cyclodextrin. The cyclodextrin component is, in general, used in an amount of 0.1 to 3.0 mol per mol of GCP acid addition salt.

Thus obtained GCP acid addition salt-cyclodextrin complex may be administered either orally or parenterally, and is useful for the treatment of ulcers. Thus, they may be administered orally in the form of tablets, capsules, granules and fine powders, or parenterally in the form of injections, suppositories and the like.

The invention shall be now more fully explained in the following Examples.

Example 1

To 600 ml of water, were added 46.3 g (0.1 mole) of (2'-benzyloxycarbonyl)phenyl trans-4-guanidinomethylcyclohexanecarboxylate hydrochloride monohydrate and 113.5 g (0.1 mole) of $\beta$-cyclodextrin, and the mixture was heated to 70°–75° C. to dissolve these components. This solution was, according to normal procedure, subjected to freeze-drying to obtain a complex of (2'-benzyloxycarbonyl)phenyl trans-4-guanidinomethylcyclohexanecarboxylate hydrochloride with $\beta$-cyclodextrin. Yield 155 g.

Figure 1:
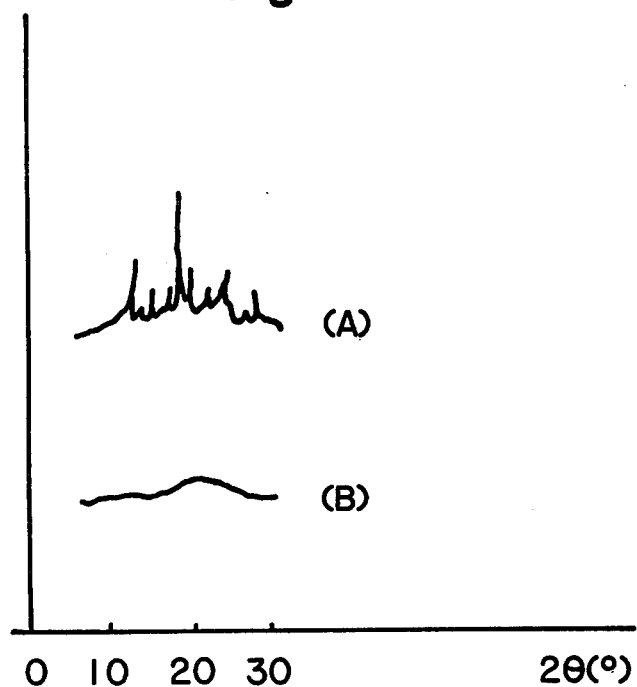

Thus obtained product was confirmed to be of amorphous structure by X-ray diffraction. That is, as shown in FIG. 1 (Powder X-ray difraction pattern), the pattern of the product (B) totally differed from the characteristic diffraction pattern of GCP HCl (A) and was apparently of amorphous structure.

It was also confirmed that TLC behavior of the product differed from that of GCP hydrochloride. That is, when developed with acetonitrile, they each showed different Rf values as shown below:

| Solvent for Developement | GCP hydrochloride | | product (complex compound) | |
|---|---|---|---|---|
| acetonitrile | Rf | 0.9 | Rf | 0.0 |

(coloring by UV)

Figure 2:
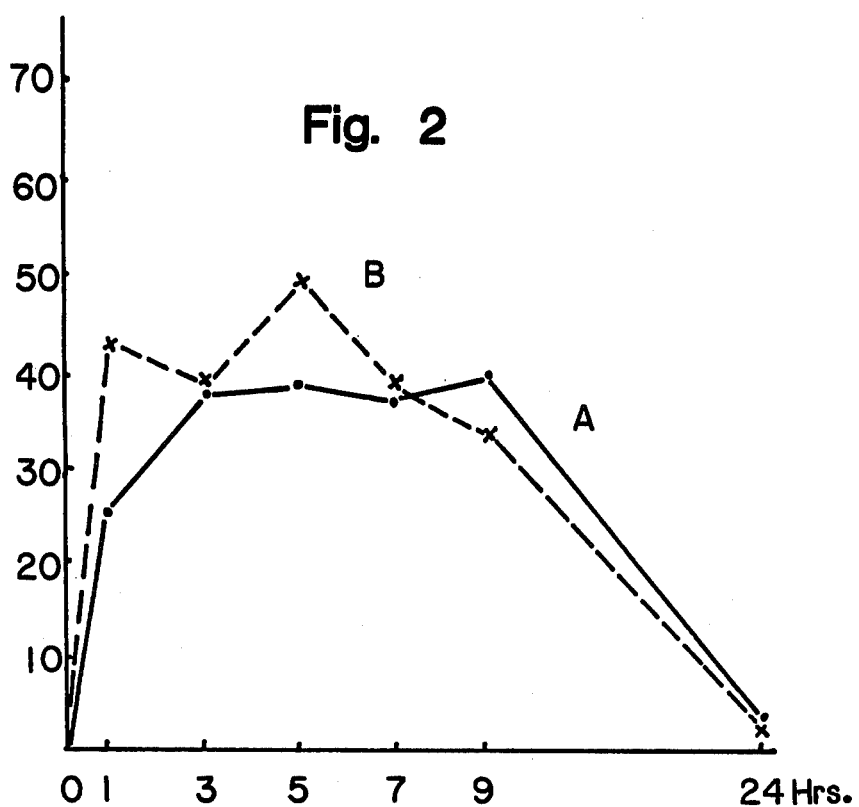
Figure 3:
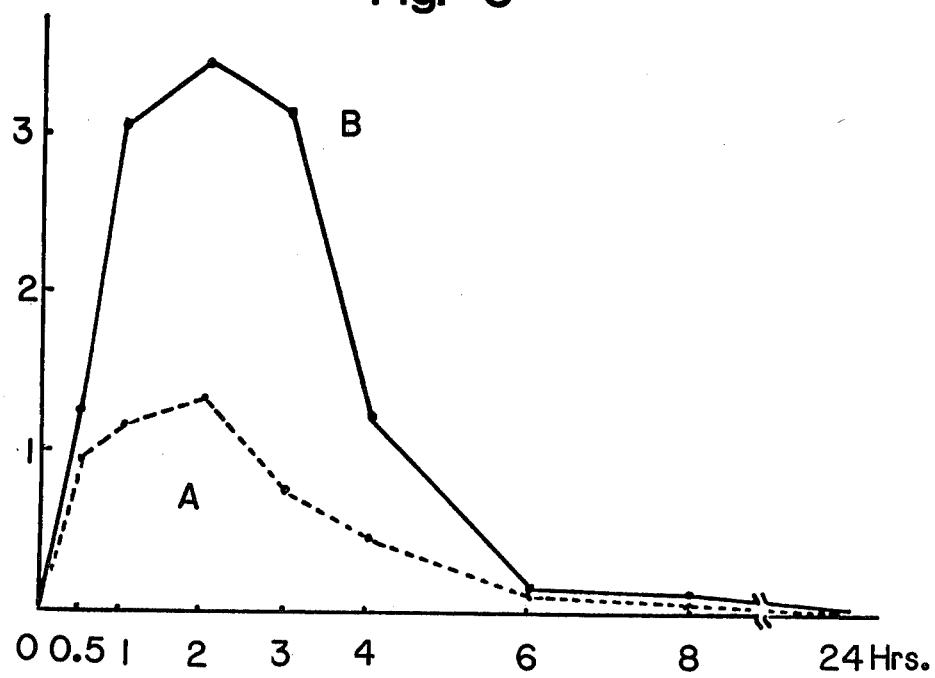

When administered orally to a group of rats, a higher blood level (see FIG. 2) was maintained for a longer duration with the present complex as compared with those of GCP hydrochloride. FIG. 2 shows variation of the salicylic acid concentration in blood plasma for GCP HCl (A) and for the complex (B), each administered in an amount of 100 mg (as GCP HCl)/Kg, (ordinate axis), with time (transverse axis). In another test, 14 C-labelled compounds were administered orally to a group of rats (dose: 100 mg/Kg, including 219 $\mu$Ci lablelled compound), and variation of GCP HCl eq. in blood with time was determined. FIG. 3 shows the results thereof, wherein the ordinate axis indicates GCP HCl eq. ($\mu$g/ml) and the transverse axis shows time (hour).

Pharmacological test results are shown below:

In each test, a group of rats were used and averaged test results were shown.

(a) Inhibition of stress ulcer (water dipping method):

| | administration dosage mg/kg | coefficient of ulceration | inhibition % |
|---|---|---|---|
| control | | 25.8 ± 2.9 | |
| complex | 320.5 | 23.3 ± 2.4 | 9.7 |
| | 641.0 (200) | 15.4 ± 3.1 | 40.3 |
| | 1282.1 (400) | 11.2 ± 2.3 | 56.5 |
| | 2564.1 (800) | 7.6 ± 1.3 | 70.5 |

( ) corresponding GCP hydrochloride amount

The complex was administered orally 10 minutes before the start of stressing.

(b) Inhibition of indomethacine induced ulcer:

| | administration dosage mg/kg | coefficient of ulceration | inhibition % |
|---|---|---|---|
| control | | 23.3 ± 3.4 | |
| complex | 120.0 (37.5) | 11.6 ± 3.5 | 50.2 |
| | 240.4 (75) | 5.6 ± 1.1 | 76.0 |

( ) corresponding GCP hydrochloride amount

The complex was administered orally 10 minutes before the medication with indomethacin (20 mg/kg).

(c) Effect on secretion of gastric juice:

| | admin. dosage mg/kg | amount of gast. juice ml | inhibition % | acid amount μEq/hr | inhibition % |
|---|---|---|---|---|---|
| control | | 7.0 ± 0.6 | | 94.6 ± 13.2 | |
| complex | 240.4 (75) | 5.3 ± 0.7 | 24.3 | 70.6 ± 11.2 | 25.4 |
| | 961.5 (300) | 5.0 ± 0.4 | 28.6 | 67.4 ± 8.4 | 28.8 |

( ) corresponding GCP hydrochloride amount

The complex was administered into the duodenum immediately after tying the pylorus and gastric juice was collected after the elapse of 7 hours for said tying.

Example 2

10 g of (2'-benzyloxycarbonyl)phenyl trans-4-guanidinomethylcyclohexanecarboxylate hydrochloride and 14.1 g of β-cyclodextrin were suspended in 150 ml of water and heated. At 75° C., a clear solution was obtained, which was, after keeping it at the same temperature for 30 minutes, concentrated under reduced pressure to obtain a solid product. After washing with acetonitrile and drying, 14.4 g of complex product were obtained.

Figure 4:
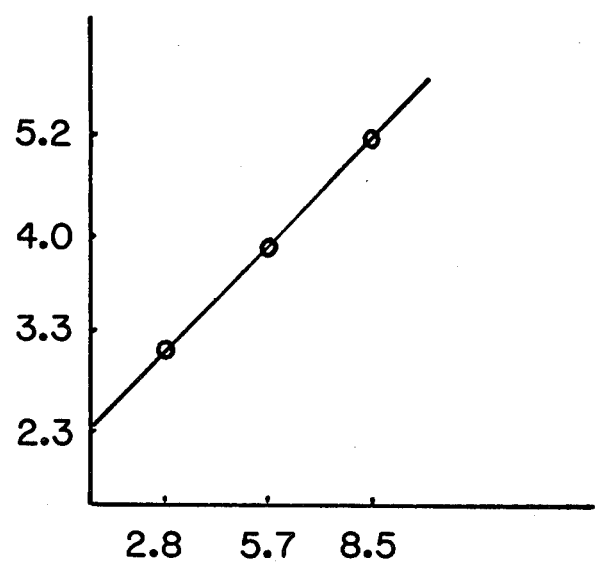

FIG. 4 is a Phase Solubility Diagam (in water, at 25° C.), wherein the ordinate axis shows GCP HCl amount (mg/ml) and the transverse axis is β-cyclodextrin amount (mg/ml).

What is claimed is:

1. A complex of an acid addition salt of (2'-benzyloxycarbonyl)phenyl trans-4-guanidinomethylcyclohexanecarboxylate with a cyclodextrin.

2. The complex according to claim 1, wherein the acid addition salt is a member selected from the group consisting of hydrochloride, hydrobromide, hydroiodide, carbonate, acetate, sulfate, p-toluenesulfonate, methanesulfonate, lactate, maleate, fumarate, tartarate, and citrate.

3. The complex according to claim 1, wherein the cyclodextrin is a member selected from the group consisting of α-cyclodextrin, β-cyclodextrin and γ-cyclodextrin.

4. The complex according to claim 1, which is obtained from (2'-benzyloxycarbonyl)phenyl trans-4-guanidinomethylcyclohexanecarboxylic hydrochloride and β-cyclodextrin.

5. A pharmaceutical composition useful for treating ulcers, comprising as an active ingredient a complex of an acid addition salt of (2'-benzyloxycarbonyl)phenyl trans-4-guanidinomethylcyclohexanecarboxylate with a cyclodextrin, and a pharmaceutically acceptable carrier therefor.

6. The composition according to claim 5, wherein the acid addition salt is a member selected from the group consisting of hydrochloride, hydrobromide, hydroiodide, carbonate, acetate, sulfate, p-toluenesulfonate, methanesulfonate, lactate, maleate, fumarate, tartarate, and citrate.

7. The composition according to claim 5, wherein the cyclodextrin is a member selected from the group consisting of α-cyclodextrin, β-cyclodextrin and γ-cyclodextrin.

8. The composition according to claim 5, wherein the complex is formed by the reaction of (2'-benzyloxycarbonyl)phenyl trans-4-guanidinomethylcyclohexanecarboxylate hydrochloride and β-cyclodextrin.

* * * * *